(12) United States Patent
Schneebeli

(10) Patent No.: US 6,197,572 B1
(45) Date of Patent: Mar. 6, 2001

(54) THERMAL CYCLER HAVING AN AUTOMATICALLY POSITIONABLE LID

(75) Inventor: Rolf Schneebeli, Mettmenstetten (CH)

(73) Assignee: Roche Diagnostics Corporation, Indianapolis, IN (US)

(*) Notice: Subject to any disclaimer, the term of this patent is extended or adjusted under 35 U.S.C. 154(b) by 0 days.

(21) Appl. No.: 09/302,713

(22) Filed: Apr. 30, 1999

(30) Foreign Application Priority Data

May 4, 1998 (EP) .................................. 98810400

(51) Int. Cl.[7] .................................................. C12M 1/40
(52) U.S. Cl. ........................... 435/286.2; 435/287.2; 435/303.1; 435/305.3; 435/288.4
(58) Field of Search ........................... 435/286.1, 286.2, 435/287.2, 287.3, 288.4, 288.7, 303.1, 305.3, 305.4, 809; 422/63, 65, 68.1, 102, 104

(56) References Cited

U.S. PATENT DOCUMENTS

| | | |
|---|---|---|
| 5,282,543 | 2/1994 | Ralph et al. . |
| 5,496,517 * | 3/1996 | Pfost et al. .................. 422/63 |
| 5,496,518 | 3/1996 | Kenji et al. . |
| 5,556,958 | 9/1996 | Carroll et al. . |
| 5,616,301 | 4/1997 | Rolf et al. . |

FOREIGN PATENT DOCUMENTS

| | | |
|---|---|---|
| 0 311 440 | 4/1989 | (EP) . |
| 0 542 422 * | 5/1993 | (EP) . |
| 0 628 823 | 12/1994 | (EP) . |
| 0 810 030 | 12/1997 | (EP) . |

* cited by examiner

Primary Examiner—William H. Beisner
(74) Attorney, Agent, or Firm—Gibbons, Del Deo Dolan, Griffinger & Vecchione (57) ABSTRACT

This invention involves a thermal cycler capable of performing amplification of nucleic acids. This thermal cycler provides for the fully automatic positioning of its movable lid, which can be placed in two positions. The lid is also suitable for heating a plurality of reaction vessels and for shielding them from light from the environment. In addition, the thermal cycler also includes a thermal block having a plurality of chambers each of which receives the lower part of a reaction vessel. Finally, the thermal cycler has a lid carrier for moving the lid from the first position to the second position and vice versa.

8 Claims, 10 Drawing Sheets

THERMAL CYCLER HAVING AN AUTOMATICALLY POSITIONABLE LID

RELATED APPLICATIONS

This application is related to the European Patent Application No. 98810400.6 filed on May 4, 1998.

BACKGROUND OF THE INVENTION

1. Field of the Invention

The present invention refers to a thermal cycler for performing amplification of nucleic acids, e.g. by means of a polymerase chain reaction (PCR).

2. Description of the Prior Art

Thermal cyclers of the above-mentioned kind have a heated lid which is positioned manually to cover a plurality of reaction vessels positioned in chambers of a thermal block of the thermal cycler during thermal cycling of sample-reaction-mixtures contained in the reaction vessels. The lid is also manually removed in order to have access to the reaction vessel after the end of the thermal cycling. Known lids of the latter type have a key disadvantage. They are not suitable for automatic change of their position with respect to the thermal block.

SUMMARY OF THE INVENTION

It is an object of the present invention to provide a thermal cycler comprising a heated lid which is automatically positionable to cover and uncover a plurality of reaction vessels positioned in the chambers of a thermal block of the thermal cycler. In addition the heated lid should be suitable to ensure that when the reaction vessels are covered by the heated lid then no external light can reach the interior of the reaction vessels.

According to the invention this aim is achieved with a thermal cycler of the above mentioned kind which comprises:

a thermal block having a plurality of chambers each of which can receive the lower part of a reaction vessel;

a movable lid having heating means positioned within it, said lid having a surface that can cover said thermal block and said reaction vessels positioned in said chambers thereof so that said lid fully shields said vessels from light in the environment of said thermal cycler, said lid being positionable at a first position at which it covers said thermal block and said reaction vessels positioned in said chambers thereof, and at a second position at which said lid does not cover said thermal block and said reaction vessels positioned in said chambers thereof, and transport means for moving said lid from said first position to said second position and vice versa, said transport means being so configured and dimensioned that the path followed by said lid as it is moved from said second position to said first position comprises a first path segment which lies above and at a predetermined distance from said thermal block and along which said lid is moved towards a stopper until it abuts against said stopper, and a second path segment along which said lid is moved downwards until it is vertically aligned with said thermal block and exerts a predetermined pressure on said reaction vessels positioned in said chambers of said thermal block.

The thermal cycler of the present invention achieves the above mentioned objectives. In addition, the configuration of the lid and of the mechanism for moving it makes it suitable for obtaining optimum results with regard to both suitable heating effect on the reaction vessels and with regard to automatic processing thereof.

DETAILED DESCRIPTION OF THE INVENTION

The present invention refers to a thermal cycler for performing amplification of nucleic acids.

Figure 1:
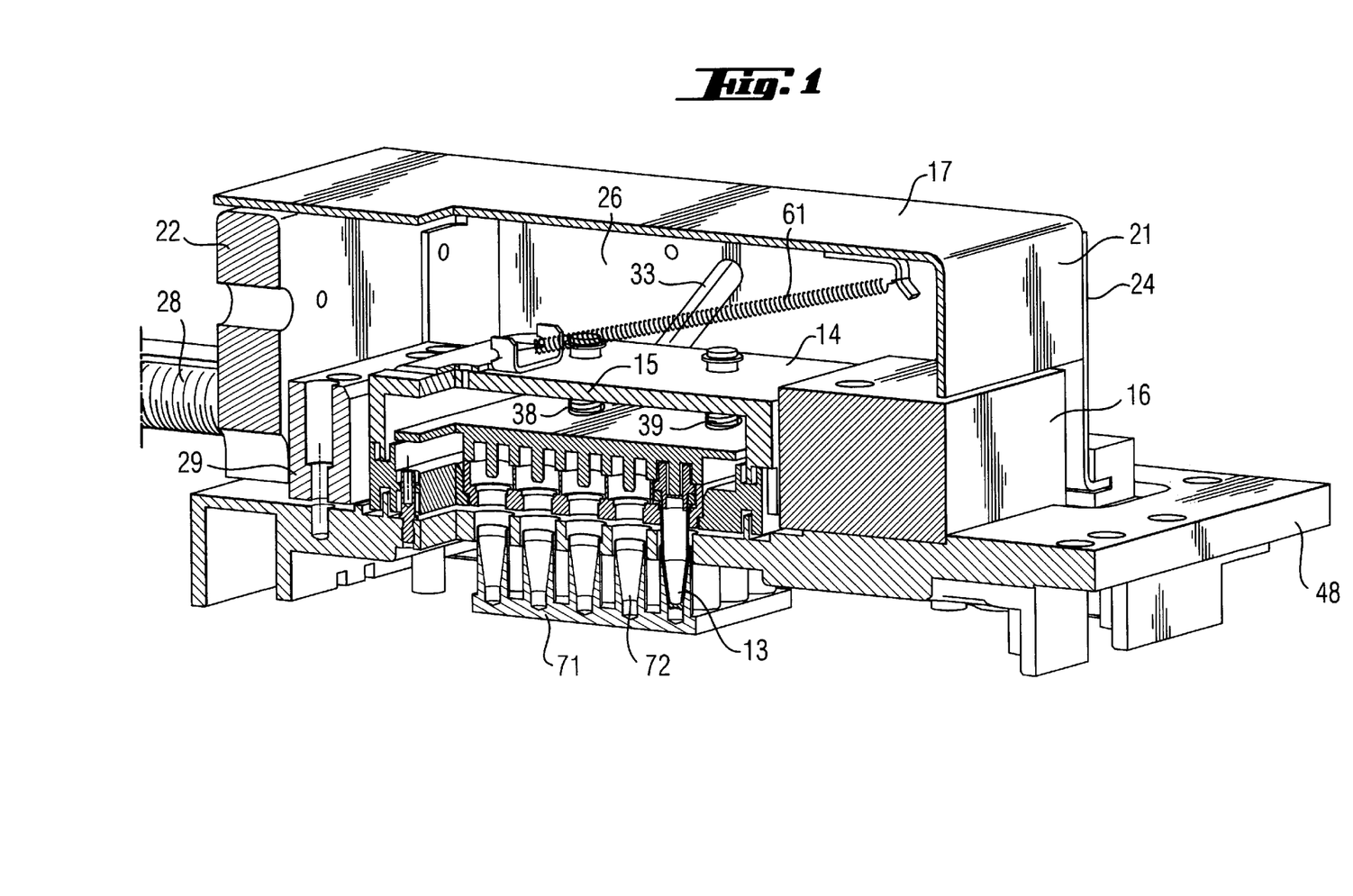
FIG. 1 is a perspective, cross-sectional view of a thermal cycler with the movable lid at a first position.

As shown in FIG. 1 an embodiment of a thermal cycler according to the present invention comprises a metallic thermal block 71 mounted on a base 48, a movable lid 14, and transport means for moving the lid 14. The reaction vessels 13 containing suitable sample-reagent mixtures and closed by caps are positioned on thermal block 71. The reaction vessels 13 and their caps are preferably of suitable plastic materials.

The movable lid 14 has heating means 15 which are positioned within an inner space of the lid 14, which inner space is limited by top and side walls of the lid 14. Heating means 15 are mechanically connected with lid the 14. This mechanical connection comprises pusher springs 36, 37, 38 and 39.

The thermal block 71 has a plurality of chambers 72 each of which is apt to receive the lower part of a reaction vessel 13.

The lid 14 is positionable at a first position (lid closed) at which it covers the thermal block 71 and the reaction vessels positioned in the chambers 72 thereof. The lid 14 is also positionable at a second position (lid open) at which the lid 14 does not cover the thermal block 71 and the reaction vessels positioned in the chambers 72 thereof.

The lid 14 has a surface which is apt to cover the thermal block 71 and the reaction vessels 13 positioned in the chambers 72 thereof when the lid 14 is in the above-mentioned first position (lid closed). When the lid 14 is in this position, it fully shields reaction vessels 13 from light in the environment of the thermal cycler. This light should not interfere with the measurement of fluorescence light emitted by sample-reagent-mixtures contained in the reaction vessels 13.

The transport means for moving the lid 14 from the first position (lid closed) to the second position (lid open) and vice versa are so configured and dimensioned that the path followed by the lid 14 as it is moved by the transport means from the second position (lid open) to the first position (lid closed) comprises the following path segments: (1) a first path segment which lies above and at a predetermined distance from the thermal block 71 and along which the lid 14 is moved towards a stopper 16 until it abuts against the stopper 16, and (2) a second path segment along which the lid 14 is moved downwards until it is vertically aligned with the thermal block 71 and exerts a predetermined pressure on the reaction vessels 13 positioned in the chambers 72 of the thermal block 71.

The transport means for moving the lid 14 are comprised of: a stopper 16 positioned in the above-mentioned first path segment of the movement of the lid 14; a motor driven lid carrier 17; and plates 25 and 26 mounted on the inner surface of the side walls 23 of the lid carrier 17.

The stopper 16 is mounted on the base 48 and has a plane surface 18 which is substantially perpendicular to the above-mentioned first path segment.

The lid carrier 17 has a front end wall 21 which is substantially in face of the plane surface 18 of the stopper 16, a rear end wall 22, and side walls 23 and 24 extending between the front and rear walls 21 and 22. The lid carrier 17 has means for holding the lid 14 within it when the lid 14 is in the first position.

The transport means for moving the lid 14 further comprise a motor driven spindle 28 for moving the rear wall 22 of the lid carrier 17 along the longitudinal axis of the spindle 28 in both senses, that is towards and away from the stopper 16, a spindle bearing 29 mounted on a base 48, and means (not shown) for controlling the operation of the motor (not shown) which drives the spindle 28.

The plate 25 is fixed on the inner surface of a side wall 23 of the lid carrier 17 and the plate 26 is fixed on the inner surface of the other side wall 24 of the lid carrier 17. Each of the plates 25 and 26 has a pair of guiding slots 31 and 32 respectively for guiding the movement of the lid 14 along the above-mentioned second path segment.

Figure 2:
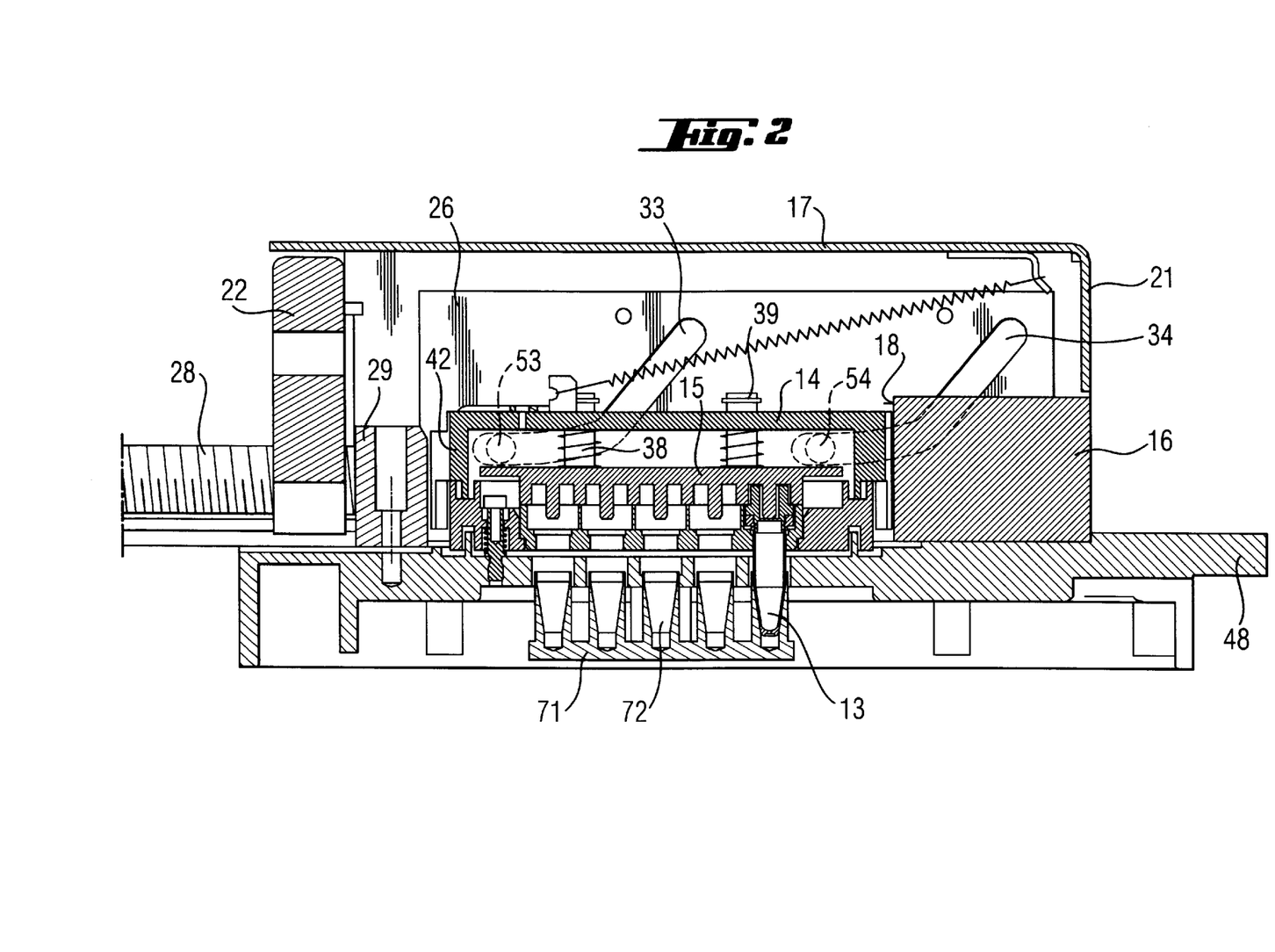
FIG. 2 is a cross-sectional view of the thermal cycler.
Figure 3:
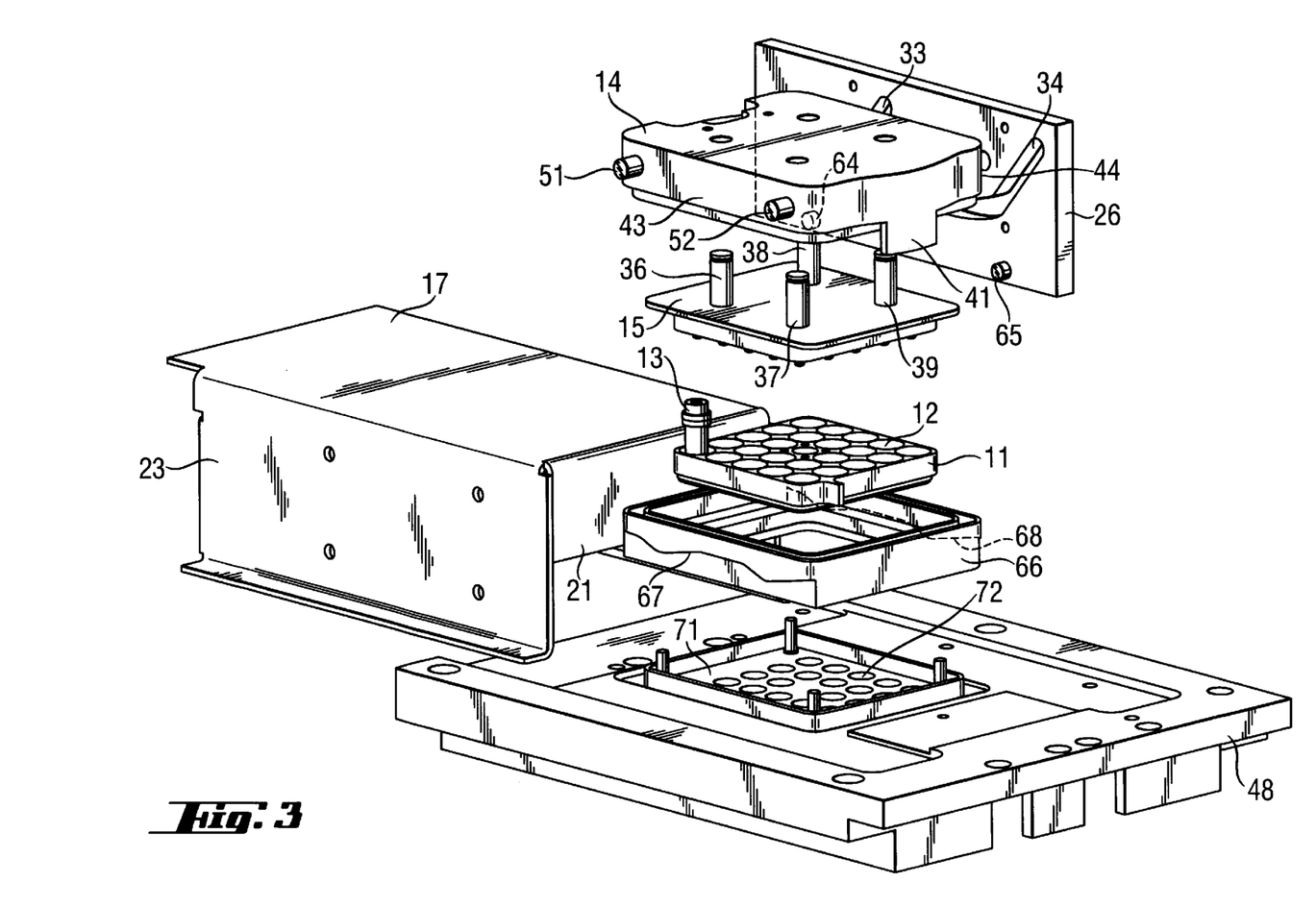
FIG. 3 is a perspective exploded view showing parts of the thermal cycler.
Figure 4:
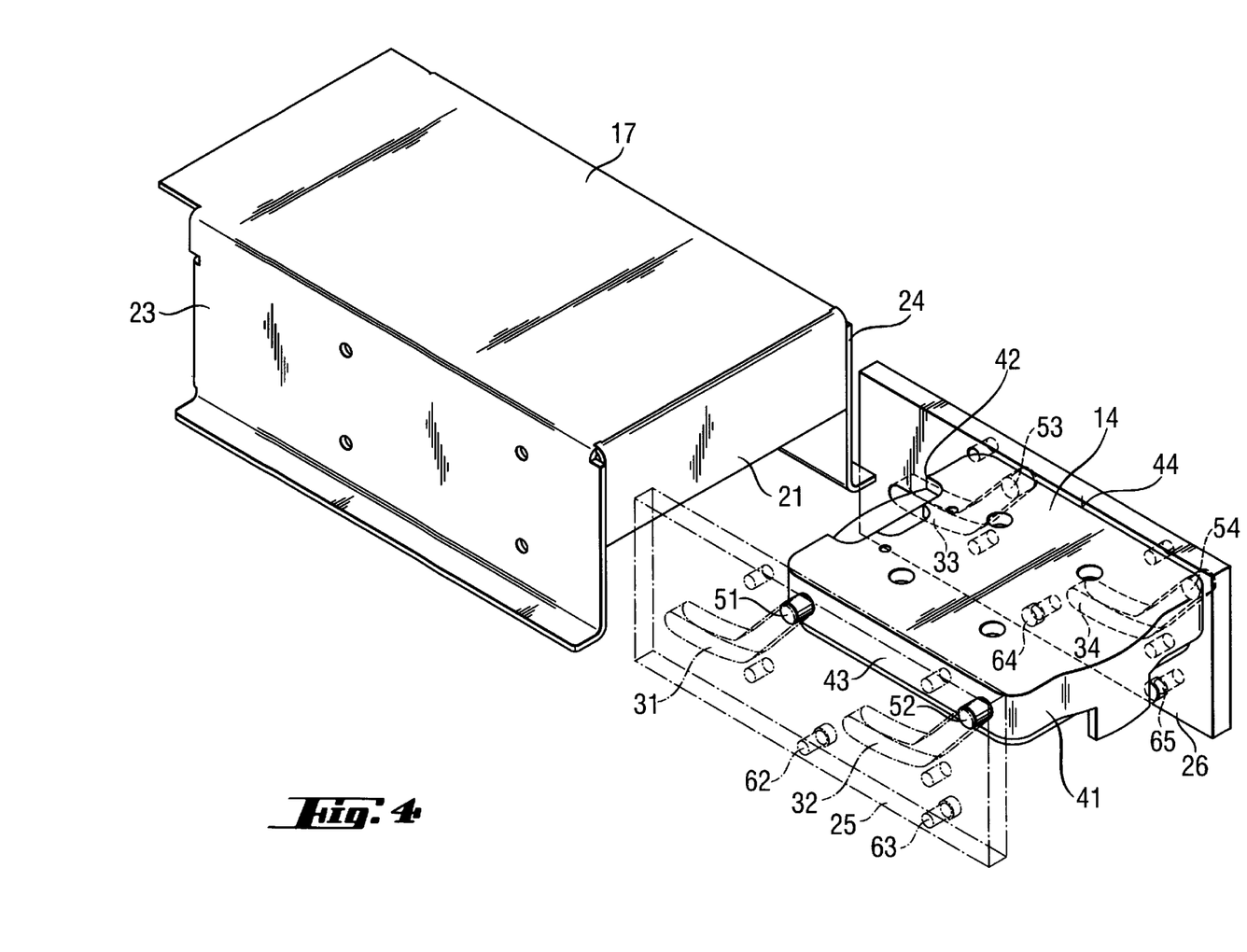
FIG. 4 is a first schematic perspective view of the movable lid and of parts of the transport means.

As shown in FIGS. 2, 3 and 4, the lid 14 has an inner and an outer top surface, a front end wall 41 which is substantially in face of the plane surface 18 of the stopper 16, a rear end wall 42, and side walls 43 and 44 extending between the front and rear walls and parallel to the side walls 23 and 24 of the lid carrier 17. The side walls of the lid 14 include outward projecting pins 51, 52, 53, 54 which fit into and slide in guiding slots 31 and 32 of the plate 25, and guiding slots 33 and 34 of the plate 26, respectively.

In a preferred embodiment, the transport means for moving the lid 14 further comprise a tension spring 61 one end of which is attached to the front end of the inner top surface of the lid carrier 17, whereas the other end of the spring 61 is attached to the rear part of the top surface of the lid 14.

Figure 5:
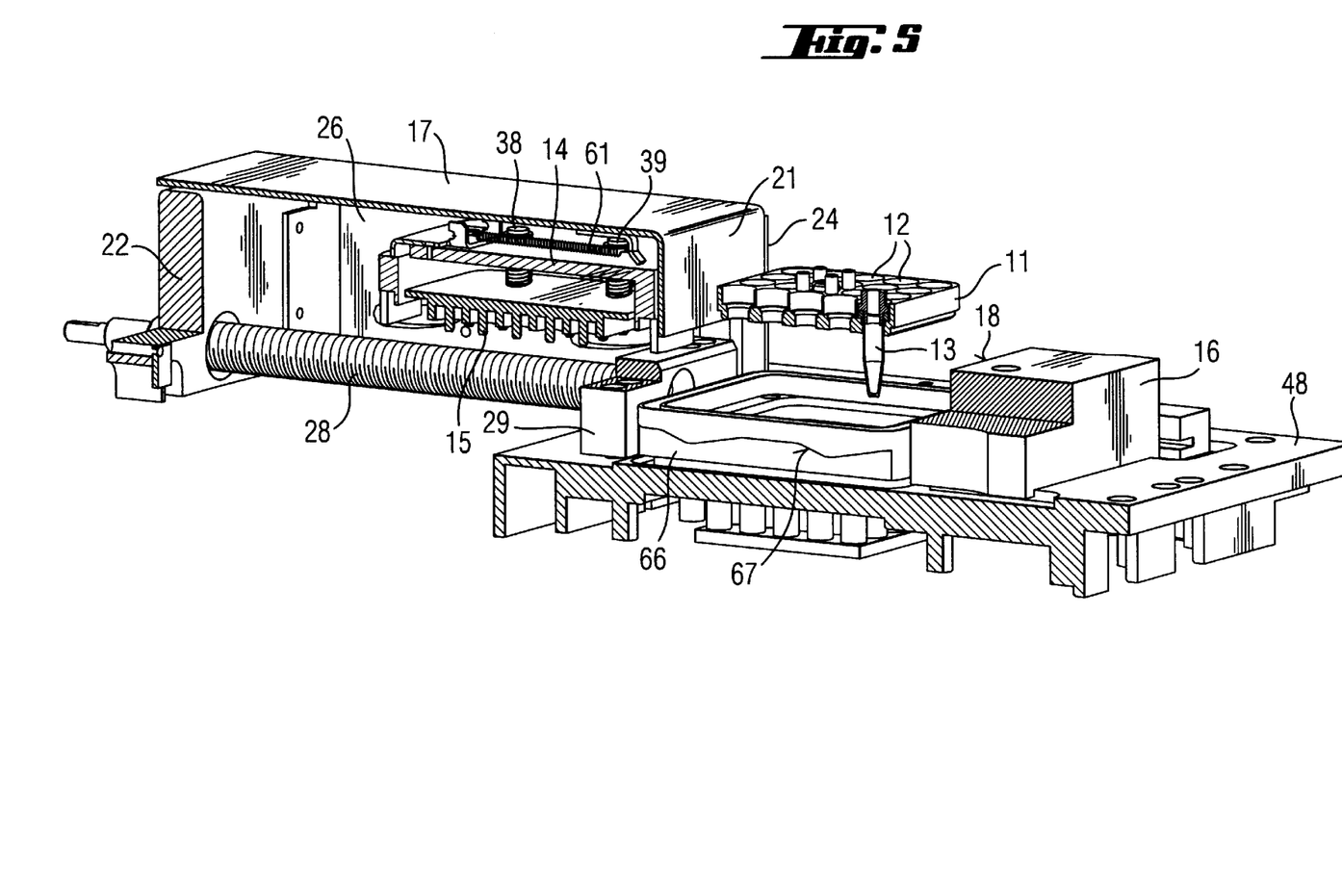
FIG. 5 is a perspective view, partially in cross-section, of the thermal cycler with the movable lid is at a second position.
Figure 6:
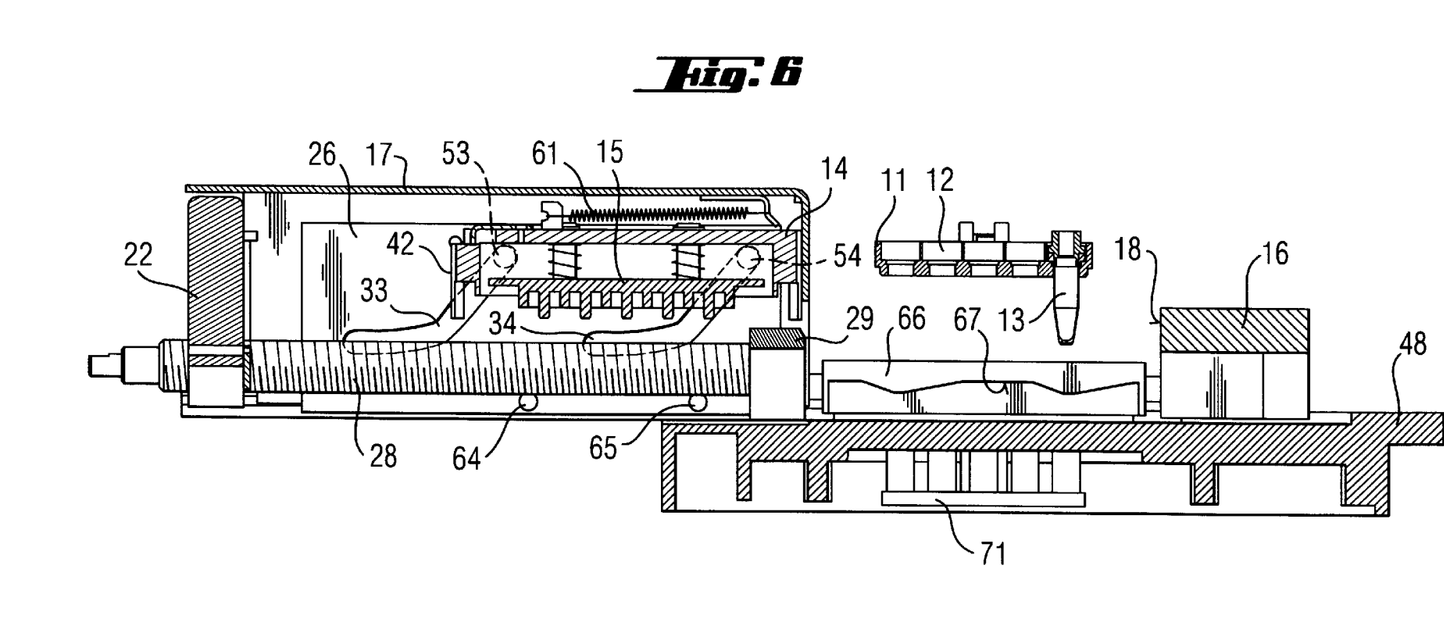
FIG. 6 is a cross-sectional view of the thermal cycler.

The operation of the above-described transport means for moving the lid 14 is better understood by referring to FIGS. 5 and 6. These figures show the position of the lid carrier 17 when the lid 14 is in the above-mentioned second position (lid open). When lid 14 and lid carrier 17 are positioned as shown in FIGS. 5 and 6, a reaction tube holder 11 having a plurality of apertures 12 and carrying a plurality of reaction vessels 13 inserted through those apertures can be positioned on the thermal block 71 so that the lower part of each reaction vessel 13 fits into a chamber 72 of the thermal block 71.

After positioning the reaction vessels 13 on the thermal block 71, motion of the lid 14 from its second position (lid open) to its first position (lid closed) is initiated by horizontal displacement of the lid carrier 17 towards the stopper 16 by rotation of the spindle 28 in a first sense. In this way, the lid 14 is moved horizontally towards the stopper 16 until front end wall 41 of the lid 14 abuts against the plane surface 18 of the stopper 16. After this point of the movement of the lid 14 and since lid 14 cannot move further in the horizontal direction, further displacement of the lid carrier 17 towards the stopper 16 causes a downwards displacement of the lid 14 away from the top wall of the lid carrier 17. During this displacement of the lid 14, the tension spring 61 is stretched and the movement of the lid 14 is guided by the sliding of pins 51, 52 and 53, 54 along guiding slots 31, 32, 33 and 34 respectively. The lid 14 is displaced in this sense until heating means 15 carried by the lid 14 abut on the caps of the reaction vessels 13 and exert on these caps a predetermined pressure. At this point, the lid 14 has reached its first position (lid closed) represented in FIGS. 1 and 2.

The predetermined pressure exerted by the heating means 15 on the caps of the reaction vessels 13 when the lid 14 is at its first position (lid closed) is determined by the last part of the downwards displacement of the lid 14 guided by the lower part of the slots 31, 32, 33 and 34 and also by the mechanical characteristics of the pusher springs 36 to 39.

Figure 7:
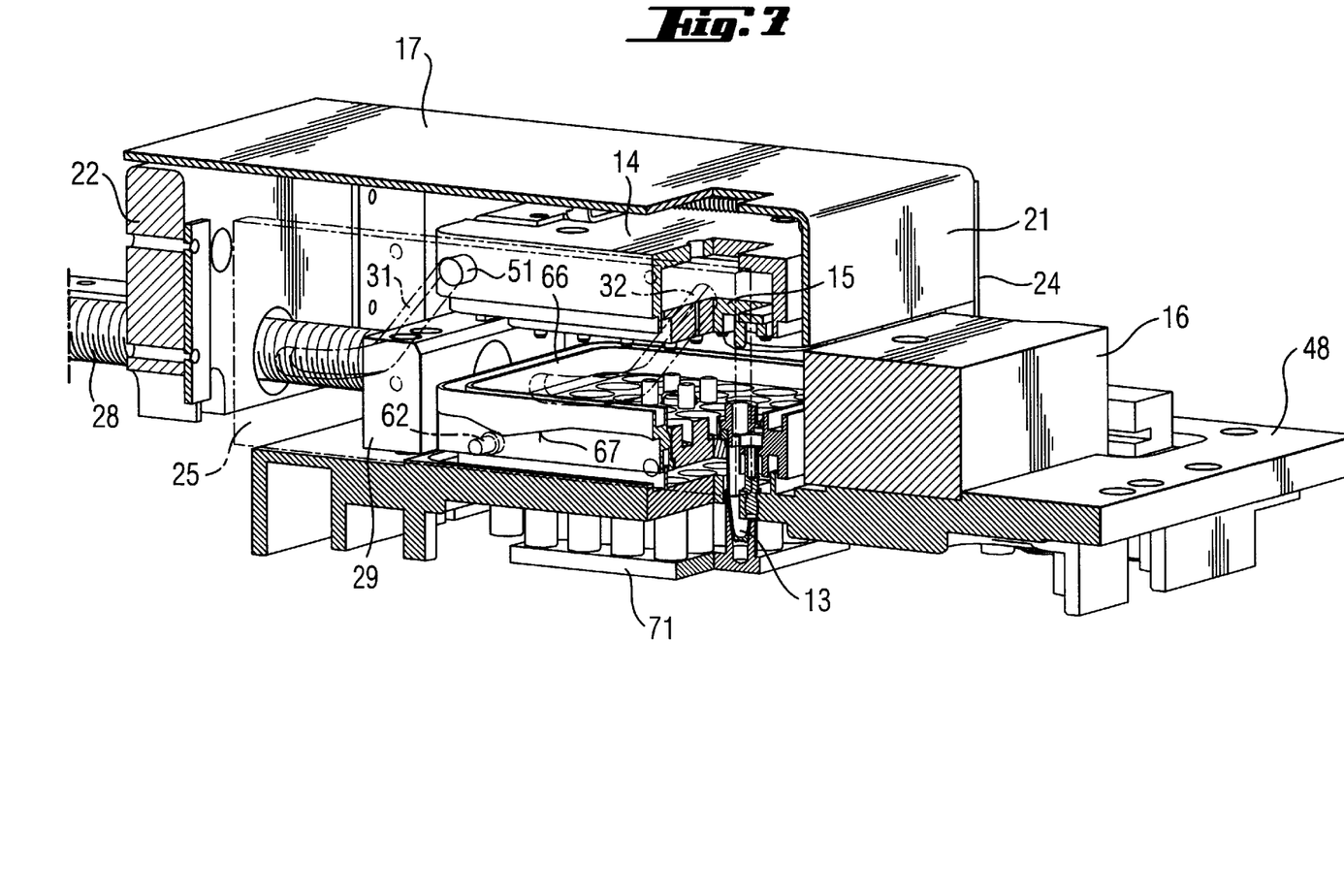
FIG. 7 is a perspective view, partially in cross-section, of the thermal cycler with the movable lid at an intermediate position between a first position and a second position.
Figure 8:
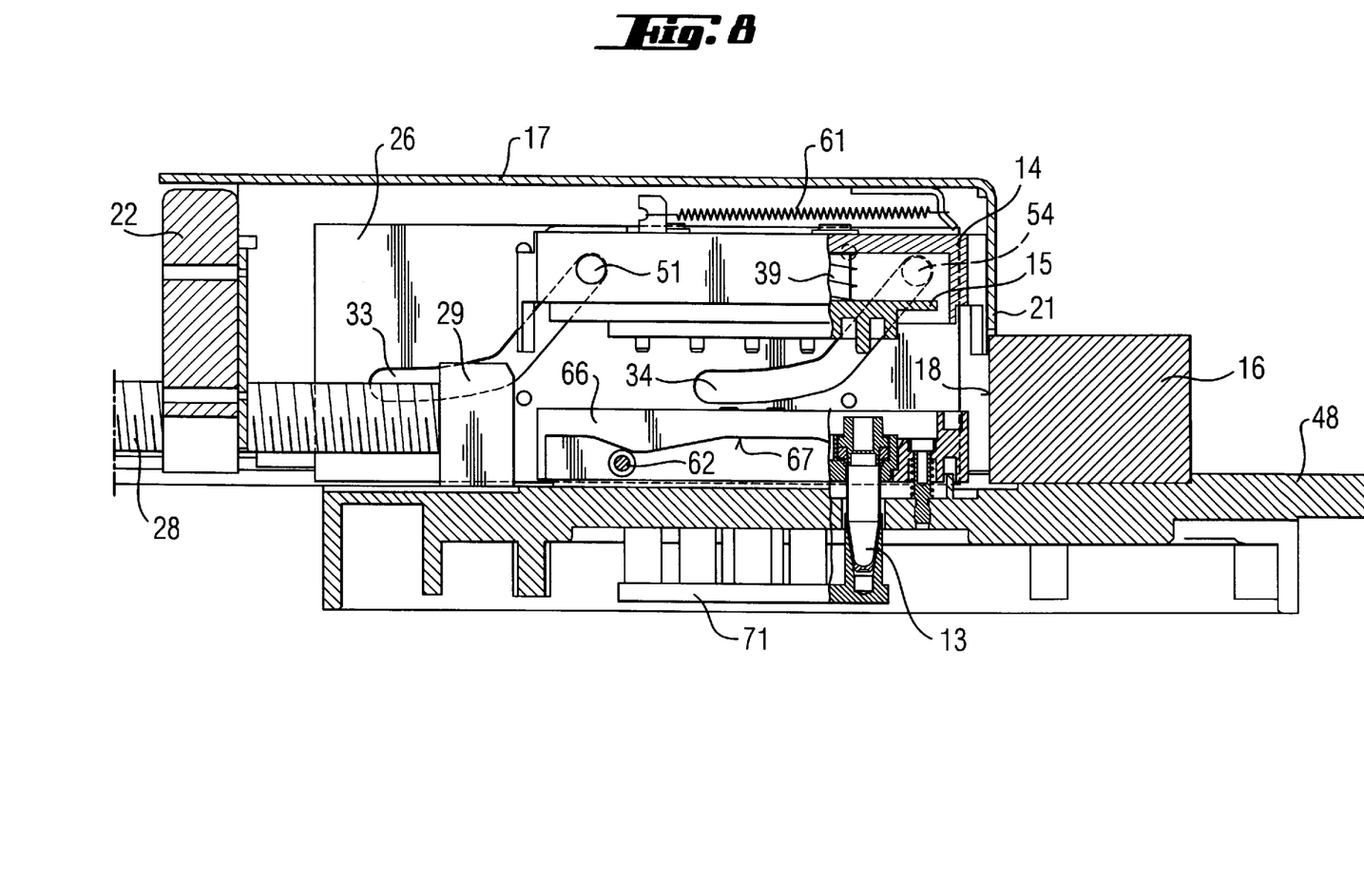
FIG. 8 is a cross-sectional view of the thermal cycler.

FIGS. 7 and 8 illustrate the position of the lid carrier 17 and other related parts of the transport system for moving the lid 14, at the point of time where front end wall 41 of the lid 14 abuts against the plane surface 18 of the stopper 16. At that point, the direction of the motion of the lid 14 changes from a horizontal motion towards the lid carrier 17 to a downward motion away from the stopper 16.

To bring the lid 14 from its first position (lid closed) to its second position (lid open), the lid carrier 17 is moved away from the stopper 16 by rotation of the spindle 28 in a second direction opposite to the first. This causes motion of the lid 14 along the same path described above, but in the reverse direction. Pulled by tension the spring 61 and guided by the slots 31, 32, 33 and 34 the lid 14 moves initially upwards towards the top wall of the lid carrier 17 and towards the stopper 16 until the lid 14 is again within the lid carrier 17 and close to the top wall thereof. After that the lid 14 moves with the lid carrier 17 further away from the stopper 16 until the lid 14 and the lid carrier 17 reach their positions shown by FIGS. 5 and 6.

In a further preferred embodiment, the transport means for moving the lid 14 further comprise ejector means 62, 63, 64, 65, 66 and 67 for separating or removing the lower part of the reaction vessels 13 from the chambers 72 of thermal block 71 when the transport means move the lid 14 from the second position to the first position. The need for such ejector means arises from the fact that at the end of a thermal cycling process the lower parts of the reaction vessels 13 tend to remain stuck in the chambers 72 of the thermal block 71.

The above-mentioned ejector means comprise an ejector frame 66 which receives the reaction vessel holder 11 and which is arranged between the latter holder and the thermal block 71. The ejector frame 66 has on the outer surface of its side walls ramp guides 67 and 68 which enter into contact with the inwards projecting pins 62, 63, 65 and 66 of the plates 25 and 26 when the lid carrier 17 is moved to bring the lid 14 from its first position (lid closed) to its second position (lid open).

The operation of the above-described ejection means for separating reaction vessels 13 from the chambers 72 of the thermal block 71 is described herein.

Figure 9:
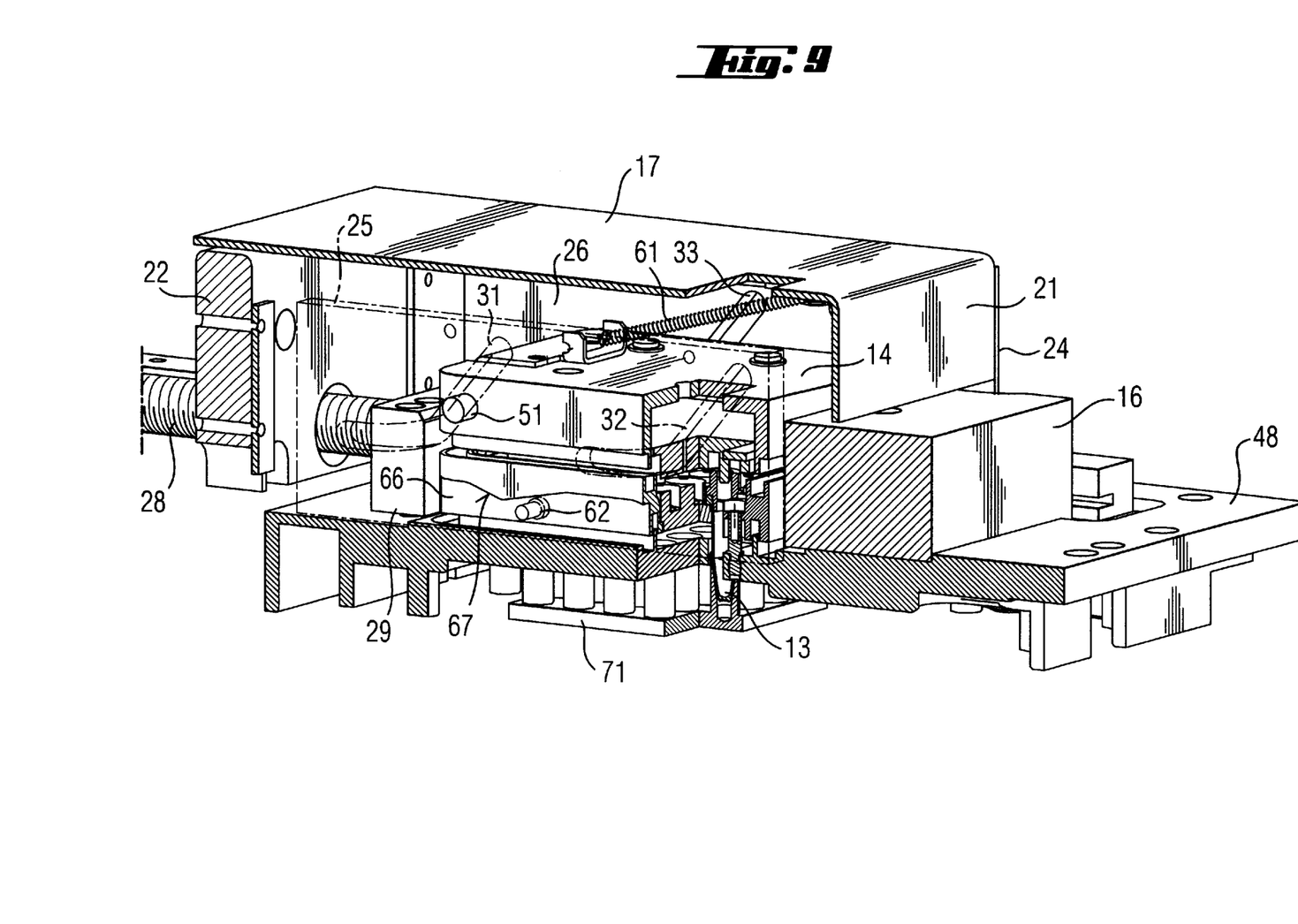
FIG. 9 is a perspective view, partially in cross-section, of the thermal cycler with the movable lid is another position.
Figure 10:
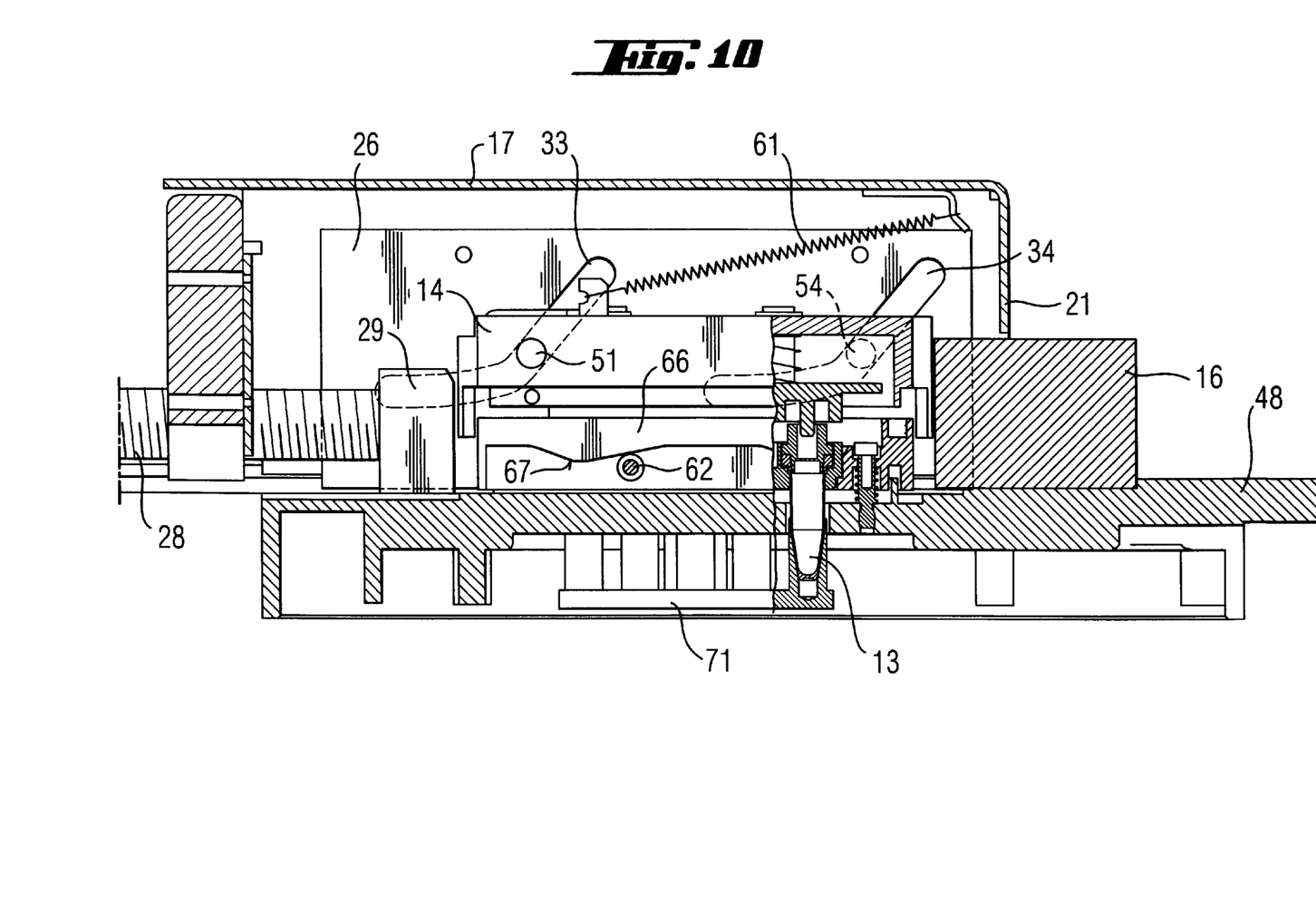
FIG. 10 is a cross-sectional view of the thermal cycler.

During the vertical upwards movement of the lid 14 as it is moved from its first position (lid closed) to its second position (lid open), relative movement of plates 25 and 26 and of pins 62 to 65 which belong to them brings these pins into contact with the ramp guides 67 and 68 of the ejector frame 66. As represented in FIGS. 9 and 10, the shape of the ramp guides 67 and 68 is such that the relative movement mentioned causes pins 62 to 65 to push the ejector frame 66 and the reaction vessel holder 11 which is positioned on the frame 66 upwards, and this causes removal of the lower parts of the reaction vessels 13 from the chambers 72 of the thermal block 71.

Within the scope of the instant invention, the thermal block 71 is used for heating and cooling the reaction vessels 13. For heating and cooling purposes, the lower part of the thermal block 71 is mechanically and thermally coupled with a Peltier element.

It should be understood, however, that the present invention herein illustrated and described is intended to be representative only, as many changes may be made therein without departing with the clear teachings of the invention. Accordingly, reference should be made to the following claims in determining the full scope of the invention, as it will be appreciated that the invention is susceptible to modification, variation and change without departing from the proper scope and fair meaning of the subjoined claims.

What is claimed is:

1. A thermal cycler for performing amplification of nucleic acids, said thermal cycler comprising:
    (a) a thermal block having a plurality of chambers each of which can receive the lower part of a reaction vessel;
    (b) a movable lid having heating means positioned within it, said lid having a surface that can cover said thermal block and said reaction vessels positioned in said chambers thereof so that said lid fully shields said vessels from light in the environment of said thermal cycler, said lid being positionable at a first position at which it covers said thermal block and said reaction vessels positioned in said chambers thereof, and at a second position at which said lid does not cover said thermal block and said reaction vessels positioned in said chambers thereof, and
    (c) transport means for moving said lid from said first position to said second position and vice versa, said transport means being so configured and dimensioned that the path followed by said lid as it is moved from said second position to said first position comprises
    a first path segment which lies above and at a predetermined distance from said thermal block and along which said lid is moved towards a stopper until it abuts against said stopper, and
    a second path segment along which said lid is moved downwards until it is vertically aligned with said thermal block and exerts a predetermined pressure on said reaction vessels positioned in said chambers of said thermal block.

2. A thermal cycler according to claim 1, wherein said transport means comprises:
    said stopper positioned in said first path segment of movement of said lid, said stopper having a plane surface which is substantially perpendicular to said first path;
    a motor driven lid carrier having a front end wall which is substantially in the face of said plane surface of said stopper, a rear end wall, and side walls extending between said front and rear walls, said lid carrier having means for holding the lid within it when said lid is in said first position; and
    a first plate fixed on the inner surface of said side wall of said lid carrier and a second plate fixed on the inner surface of said other side wall of said lid carrier, each of said first and second plates having a pair of guiding slots for guiding the movement of said lid along said second path segment.

3. A thermal cycler according to claim 2, wherein said lid has an inner and an outer top surface, a front end wall which is substantially in face of said plane surface of said stopper, a rear end wall, and side walls extending between said front and rear walls and parallel to the side walls of said lid carrier, said side walls of the lid including outwards projecting pins which can fit into and to slide in said guiding slots.

4. A thermal cycler according to claim 3, wherein said transport means further comprises a tension spring one end of which is attached to the front end of the inner top surface of said lid carrier, whereas the other end of said spring is attached to the rear part of said top surface of the lid.

5. A thermal cycler according to claim 1, wherein said transport means further includes ejector means for removing the lower part of said reaction vessels from said chambers of said thermal block when the transport means move the lid from said second position to said first position.

6. A thermal cycler according to claim 2, wherein said transport means further includes ejector means for removing the lower part of said reaction vessels from said chambers of said thermal block when the transport means move the lid from said second position to said first position.

7. A thermal cycler according to claim 3, wherein said transport means further includes ejector means for removing the lower part of said reaction vessels from said chambers of said thermal block when the transport means move the lid from said second position to said first position.

8. A thermal cycler according to claim 4, wherein said transport means further includes ejector means for removing the lower part of said reaction vessels from said chambers of said thermal block when the transport means move the lid from said second position to said first position.

* * * * *